United States Patent
Greiser

(10) Patent No.: US 10,314,512 B2
(45) Date of Patent: Jun. 11, 2019

(54) MAGNETIC RESONANCE METHOD AND APPARATUS FOR DETERMINING DEFORMATION INFORMATION FROM A CYCLICALLY MOVING EXAMINATION SUBJECT

(71) Applicant: Siemens Aktiengesellschaft, Munich (DE)

(72) Inventor: Andreas Greiser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 673 days.

(21) Appl. No.: 14/963,646

(22) Filed: Dec. 9, 2015

(65) Prior Publication Data

US 2016/0157747 A1 Jun. 9, 2016

(30) Foreign Application Priority Data

Dec. 9, 2014 (DE) .................. 10 2014 225 282

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/0037* (2013.01); *A61B 5/0044* (2013.01);
(Continued)

(58) Field of Classification Search
CPC ..... A61B 5/055; A61B 5/0037; A61B 5/7203; A61B 5/0044; A61B 2576/023;
(Continued)

(56) References Cited

U.S. PATENT DOCUMENTS 5,054,489 A 10/1991 Axel et al.
6,236,738 B1 5/2001 Zhu et al.
(Continued)

FOREIGN PATENT DOCUMENTS

| CN | 103400376 A | 11/2013 |
|----|-------------|---------|
| CN | 103761750 A | 4/2014 |
| WO | WO-92/03089 A1 | 3/1992 |

OTHER PUBLICATIONS

Fischer et al., "Improved Myocardial Tagging Contrast", Magnetic Resonance in Medicine, vol. 30:pp. 191-200 (1993).
(Continued)

Primary Examiner — Joel Lamprecht
(74) Attorney, Agent, or Firm — Schiff Hardin LLP

(57) ABSTRACT

In a magnetic resonance method and apparatus for determining an item of deformation information of an examination object that exhibits a cyclical movement within an examination subject, a spatial magnetization pattern is generated in an MR scanner, and MR signals are acquired from the subject during at least two cycles of the cyclical movement, with the spatial magnetization exhibiting differences in a subsequent cycle of the movement compared to an earlier cycle. Segmented subsequent MR images are acquired in a subsequent cycle and the examination object is localized therein. This localization of the examination object is then used to localize the examination object in segmented earlier MR images from the earlier cycle, and the item of deformation information is determined in a spatial direction from the segmented earlier MR images.

12 Claims, 3 Drawing Sheets

(51) Int. Cl.
  *G06T 7/00* (2017.01)
  *G06T 7/62* (2017.01)
(52) U.S. Cl.
  CPC .......... *A61B 5/7203* (2013.01); *G06T 7/0016* (2013.01); *G06T 7/62* (2017.01); *A61B 2576/023* (2013.01); *G06T 2207/10076* (2013.01); *G06T 2207/10088* (2013.01); *G06T 2207/30048* (2013.01)
(58) Field of Classification Search
  CPC .................. G06T 7/62; G06T 7/0016; G06T 2207/30048; G06T 2207/10088; G06T 2207/10076
  See application file for complete search history.

(56) References Cited

U.S. PATENT DOCUMENTS

| | | | |
|---|---|---|---|
| 6,865,248 | B1 | 3/2005 | Rasche et al. |
| 7,043,063 | B1 | 5/2006 | Noble et al. |
| 2004/0155653 | A1* | 8/2004 | Larson .............. G01R 33/5676 324/309 |
| 2006/0241379 | A1 | 10/2006 | Greiser et al. |
| 2013/0182935 | A1 | 7/2013 | Wang et al. |
| 2014/0133717 | A1 | 5/2014 | Kabus et al. |
| 2015/0282764 | A1 | 10/2015 | Greiser et al. |

OTHER PUBLICATIONS

Osman et al., "Imaging Longitudinal Cardiac Strain on Short-Axis Images Using Strain-Encoded MRI", Magnetic Resonance in Medicine vol. 46, pp. 324-334; (2001).

Greiser et al., "New Possibilities for Myocardial Strain Imaging using Acceleration and Iterative Reconstruction", ISMRM Abstract, 6174; (2015).

Stalder, et al.: "Cardiac Multi-Contrast CINE: Real-Time Inversion-Recovery Balanced Steady-State Free Precession Imaging with Compressed-Sensing and Motion-Propagation", ISMRM, Abstract 5667, (2014).

* cited by examiner

FIG 2
FIG 3
FIG 4
FIG 5
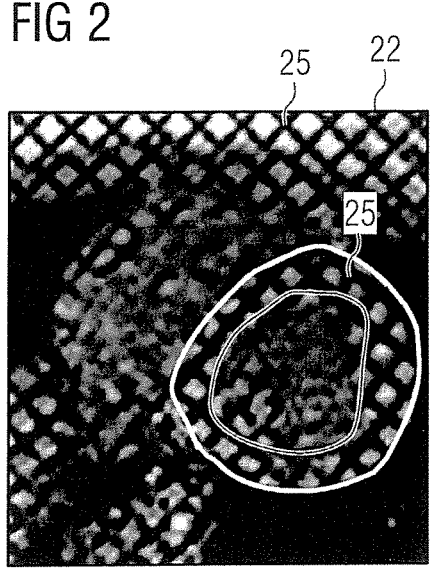
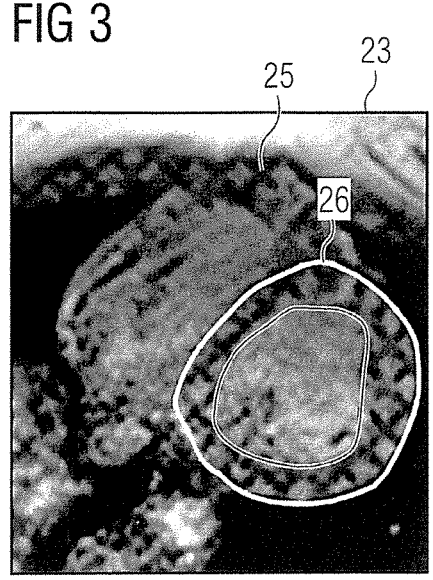
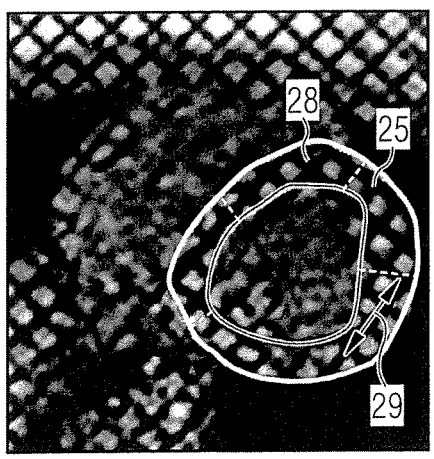
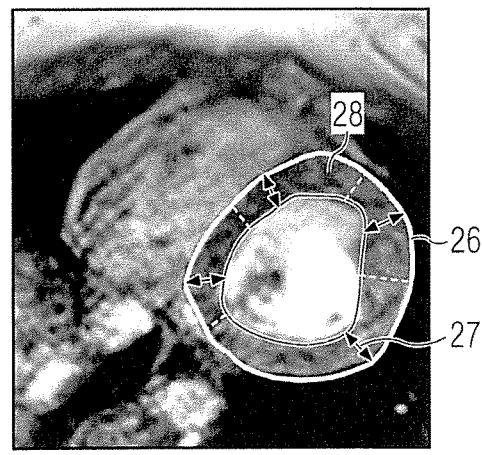

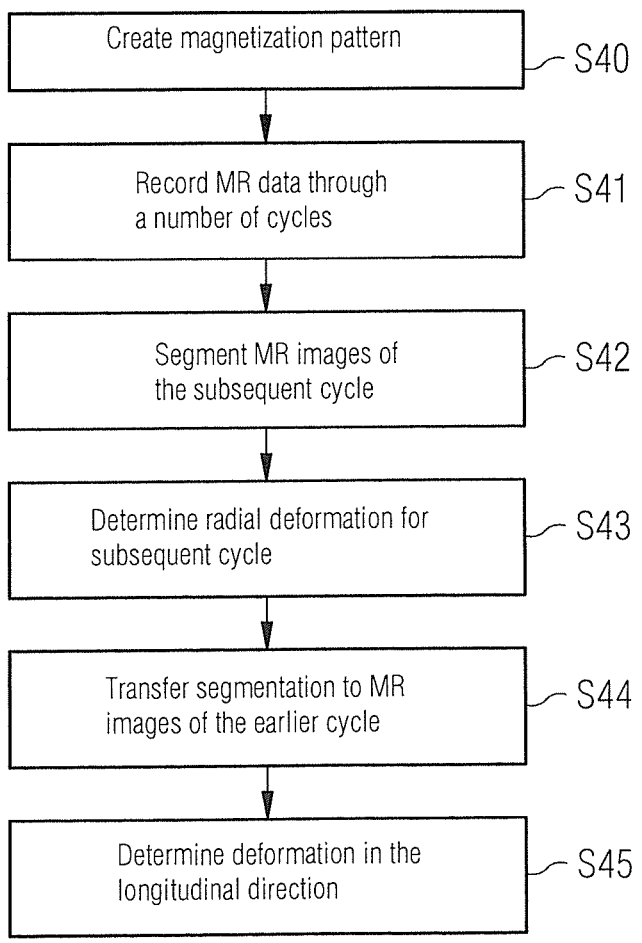

MAGNETIC RESONANCE METHOD AND APPARATUS FOR DETERMINING DEFORMATION INFORMATION FROM A CYCLICALLY MOVING EXAMINATION SUBJECT

BACKGROUND OF THE INVENTION

Field of the Invention

The present invention concerns a method for determining deformation information in an examination object that executes a cyclical movement, and to a magnetic resonance (MR) system for implementing such a method.

Description of the Prior Art

When MR images of a moving organ are recorded, such as heart or the liver, the organ's own motion must be taken into account, and possibly the movement of the entire organ due to the movement of the surrounding area. One possibility for imaging moving objects is known as the single-shot technique, in which the raw data space of an associated MR image is entirely read out after radiating a single RF pulse sequence and in which the recording of the MR data is sufficiently fast to freeze the movement. In a further recording technique known as segmented recording, the data recording for an MR image is divided over several movement cycles and the MR data are recorded only in comparable movement phases. During heart imaging, the breathing and the heart movement must be taken into account, and the movement can be minimized by means of a breath-hold technique or can be frozen by a navigator gating. A further possibility for recording such data is known as the cine data recording for measuring the myocardial muscle movement, in which a number of MR images per heart cycle are recorded with as good a contrast as possible between the myocardial muscle and blood, so that a type of movie of the heart movement is produced.

One parameter of interest when recording moving examination objects is the determination of a deformation of the moving examination object. For instance, a deformation in the peripheral direction of the myocardium and an item of radial deformation information can be determined as deformation information of the myocardium. A conclusion as to the vitality of the myocardium in the corresponding areas can be made from the deformation information in individual areas of the myocardium. During the recording of the myocardium in the short axis section, it is nevertheless difficult to calculate a deformation of the myocardium in the peripheral direction for different segments of the myocardium, because sufficient markers are not present in the myocardium on the basis of which a deformation can be estimated in the peripheral direction. This applies as well to the longitudinal deformation in the longitudinal axis sections of the heart.

It is also known to subject the magnetization to a spatial magnetization pattern such as a grid pattern. With such methods, also known as tagging methods, the examination object appears with a strip or grid pattern in the MR image. This pattern can also be used to determine the deformation information, but a radial determination of the deformation information is difficult, because there are not sufficient marker points in the radial direction.

When determining the deformation information of the myocardium or any other moving examination object, the myocardium must be reliably identified in the MR images and separated from other tissue. The segmentation of the moving object such as the myocardium that is required in the MR images is particularly difficult in MR images in which a spatial magnetization pattern was applied with the tagging method.

SUMMARY OF THE INVENTION

An object of the present invention is to further improve the determination of an item of deformation information in a moving examination object.

According to a first aspect of the invention, a method for determining an item of deformation information in an examination object is provided, wherein the examination object executes a cyclical movement, and wherein the item of deformation information is determined with the use of an MR system. A spatial magnetization pattern with spatial magnetization differences is generated during the magnetization nuclear spins of the examination object. Moreover, MR signals of the examination object are detected in order to record MR images of the examination object during at least two cycles of the cyclical movement after generating the spatial magnetization pattern. Here the spatial magnetization differences are less in a subsequent cycle of the at least two cycles than in an earlier cycle of the at least two cycles. Segmented subsequent MR images are determined with the aid of the MR images of the examination object which were recorded in the subsequent of the at least two cycles, in order to localize the examination object in the segmented subsequent MR images. Moreover, segmented earlier MR images are determined with the use of MR images of the examination object which were recorded in the earlier of the at least two cycles, using the localized examination object in the segmented subsequent MR images. Moreover, a first item of deformation information, which describes the deformation of the examination object in a first spatial direction, is determined on the basis of the segmented earlier MR images.

The magnetization following the generation of the spatial magnetization pattern approaches an equilibrium state during the at least two cycles of the cyclical movement, so that the spatial magnetization pattern and the associated magnetization differences in the MR images of the subsequent cycle are lower. It is easier to localize the examination object in these images by using segmentation algorithms. In the earlier MR images of the examination object which were recorded in the earlier of the at least two cycles, the magnetization pattern is present more significantly, so that a segmentation in order to identify the examination object is more difficult. In accordance with the invention, the localization of the examination object is transferred by the segmented subsequent MR images to the earlier MR images, and as a result segmented earlier MR images can be determined easily. The segmented earlier MR images, in which the spatial magnetization pattern is identified more easily, can be used to determine an item of deformation information. Sufficient markers in the examination object are present in the different spatial directions due to the spatial magnetization pattern, so that an item of deformation information can be determined with adequate quality in the one spatial direction. This first spatial direction preferably proceeds parallel to the contours of the moving examination object.

It is also possible to determine a second item of deformation information using the segmented subsequent MR images, wherein the second item of deformation information describes at least the deformation of the examination object in a second spatial direction, which differs from the first spatial direction, and is preferably at right angles thereto. The contours of the moving examination object can be easily identified in the segmented subsequent MR images, since the magnetization differences of the spatial magnetization pattern are much less pronounced and/or have disappeared. If the contours are easily identified, it is also possible to determine a deformation in the direction at right angles to the contours. It is possible, for instance, to determine an item of deformation information at right angles to the contours in the segmented subsequent MR images, while an item of deformation information parallel to the contours can be determined better in the segmented earlier MR images, since the spatial magnetization differences or the spatial magnetization pattern occurs more significantly here. It is thus possible in this embodiment to achieve a comprehensive item of deformation information, by the one item of information being determined on the basis of the segmented earlier MR images, and a further item of deformation information in a preferably vertical direction hereto being determined on the basis of the segmented subsequent MR images.

If the examination object is the myocardium, the first item of deformation information can describe for instance a deformation of the myocardium in the peripheral direction of the myocardium, wherein this is better determined on the basis of the segmented earlier MR images, in which the spatial magnetization pattern is more significantly present than in the MR images of the subsequent cycle. The segmentation that is required can be assumed from the segmentation of the subsequent MR images. The radial deformation information of the myocardium can be effectively taken from the segmented subsequent MR images, since on account of the more minimal magnetization differences by virtue of the pattern, the edges of the myocardium can be better identified in the MR images of the subsequent cycle.

An entire item of deformation information or an entire deformation field of the examination object can be determined from the first and the second item of deformation information. It is possible, for instance, for the entire deformation field to be determined by a weighted combination of the first item of deformation information and the second item of deformation information. The reliability with which the individual components of the deformation could be determined can be taken into account here. Moreover, the consistency of the two field components can be improved by iterative methods such as total variation methods. The two deformation fields from the "Tag" and from the "NoTag" heart cycle are available as a starting point, i.e. from the MR image with a strong magnetization pattern and with the weaker magnetization pattern, wherein the assumption is that in the "NoTag" heart cycle, e.g. the information relating to the radial deformation is more reliable than in the "Tag" deformation field. If the radial component of a myocardium pixel in the "Tag" data record is started to be replaced by the value from the "NoTag" data record, then inconsistencies result for instance from the conservation of mass (with a good spatial coverage) or the assumption of elasticity properties of the heart tissue. In a second step, the inconsistencies could then be minimized by varying the neighboring values. This can be performed successively for all myocardium pixels. Similarly, the deformation information can by contrast be transferred along the myocardium ring from the Tag heart cycle to the NoTag data record. In order to minimize inconsistencies, suitable mathematical variation methods can be used, which use the deviation from the local conservation of mass as a criterion.

The same imaging sequence can be used for the MR images in the earlier and the subsequent of the at least two cycles. It is also possible to use different imaging sequences to detect the MR signals in the two cycles. The transition from the one imaging sequence to the other imaging sequence can take place for instance in a central cycle between the two cycles, wherein the deformation information is preferably not determined in this transition cycle.

It is possible to determine and monitor the cyclical movement of the examination object. The determination of the segmentation in the MR images of the earlier cycle, i.e. a segmented earlier MR image can be calculated for an MR image of the earlier cycle, by the deformation information associated with the MR image of the earlier cycle being determined, wherein the MR image whose deformation information is most similar to the determined deformation information from the MR image of the earlier cycle is identified from the deformation information of the segmented subsequent MR images. An item of segmentation information can then be determined from the segmented subsequent MR image and transferred to the MR image of the earlier cycle with the most similar deformation information. In this embodiment, the similarity of the deformation fields in the earlier and subsequent cycle is used to transfer the segmentation information from the MR images of the subsequent cycle to the MR images of the earlier cycle. The total standard deviation between the deformation fields from the different phases can be observed for instance as a criterion for the similarity of the deformation fields for instance. The phases with the smallest standard deviation can be considered as those associated with the same heart movement state. Both movement fields contain both components. As expected, the heart movement should itself dominate the dynamics in the image series, so that the respective inaccuracies in the components are not to represent any problems in terms of this similarity consideration.

A further possibility is to transfer the segmentation of the MR images of the subsequent cycle to the MR images of the earlier cycle, by the segmented subsequent MR image being determined, which was recorded during the same time frame of the cycle as the MR image of the earlier cycle. The segmentation information from the segmented subsequent MR image can be determined and transferred to the MR image of the earlier cycle so that a segmented earlier MR image is also present.

If the examination object is the myocardium, the myocardium in the peripheral direction can be subdivided into a number of segments, wherein the two deformation components, i.e. the radial deformation and the deformation peripheral direction can be calculated for the several segments of the myocardium. As a result, a statement relating to the deformation and thus a statement relating to the vitality of the muscular tissue can be made for different myocardium segments with greater local accuracy.

The invention further concerns an MR system for determining the deformation information with an RF unit, which can generate the spatial magnetization pattern in the examination object during the signal read-out, wherein an image recording unit is provided, which is embodied to detect MR signals of the examination object in order to record MR images of the examination object during at least two cycles after generating the spatial magnetization pattern. Moreover, a computer is provided, which is configured to determine the segmented subsequent MR images in order to localize the examination object in the segmented subsequent MR images. The computer is further configured to determine segmented earlier MR images with the aid of MR images of the examination object which were recorded in the earlier of the at least two cycles, wherein these segmented earlier MR images are determined using the localized examination object in the segmented subsequent MR images. The computer can further determine the first deformation unit with the use of the segmented earlier MR images. The computer is preferably configured to determine the first item of deformation information and the second item of deformation information as described above.

BRIEF DESCRIPTION OF THE DRAWINGS

FIG. 2 is a schematic representation of an MR image, which was recorded of a myocardium as an examination object in an earlier cycle of the at least two cycles of the cyclical movement and in a subsequent cycle of the cyclical movement.

FIG. 3 is a schematic representation of a segmented myocardium for the earlier and the subsequent cycle with the magnetization pattern associated therewith.

FIG. 4 shows the myocardium shown in FIG. 2 for calculating the deformation in the longitudinal direction.

FIG. 5 shows the myocardium shown in FIG. 2 for calculating the radial deformation.

FIG. 6 is a flowchart with the basic steps for calculating an item of deformation information in accordance with the invention.

DESCRIPTION OF THE PREFERRED EMBODIMENTS

Figure 1:
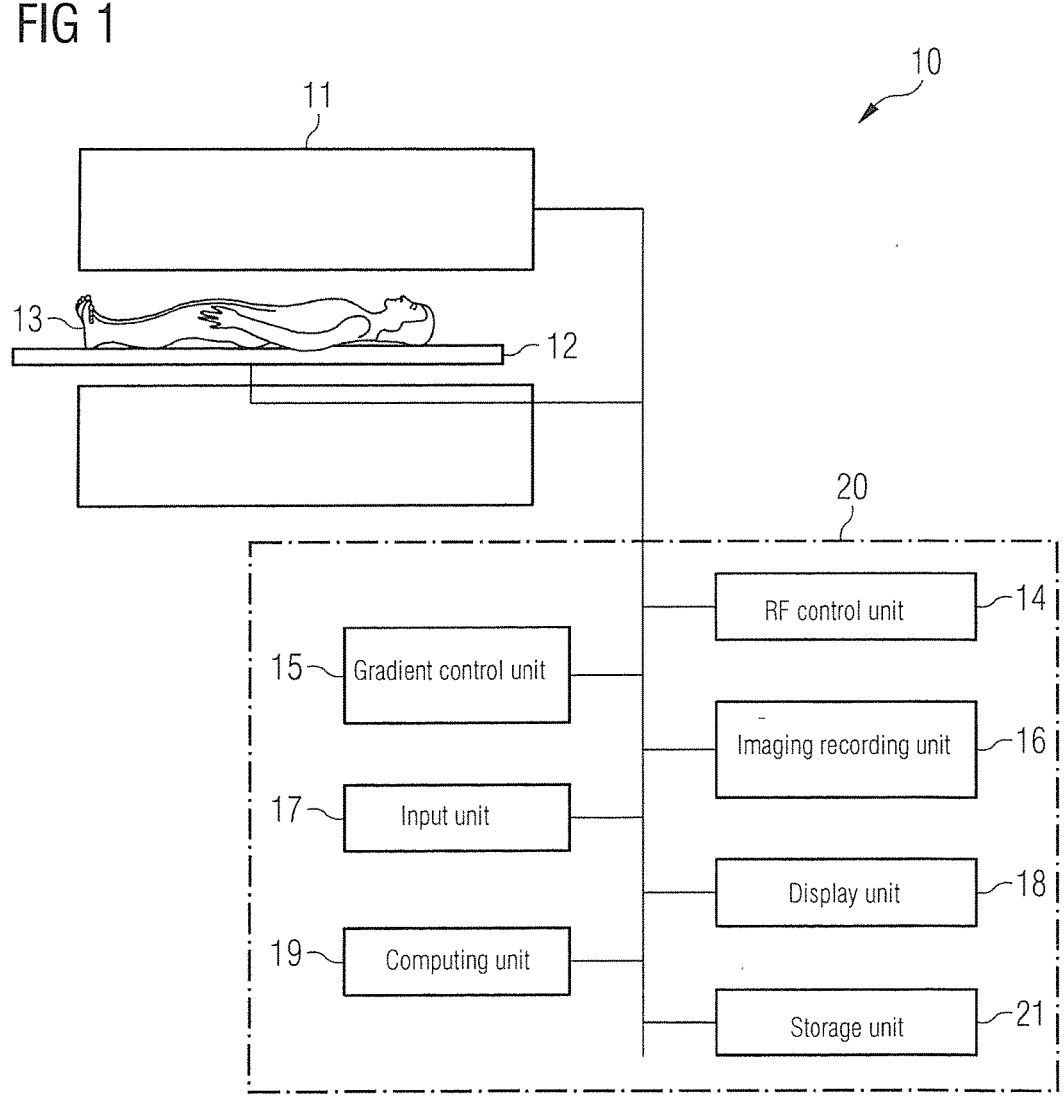
FIG. 1 schematically illustrates an MR system with which an item of deformation information of an examination object can be effectively determined.

The description below describes an MR system and a method for the operation thereof, with which an item of deformation information can easily be determined accurately in different spatial directions of a moving object such as for instance the myocardium. The individual features, which were described above and that are described again below can be used in the described context. The individual features however, also can be combined individually and with all other described features, as long as no explicit contrary description is present.

FIG. 1 is a schematic representation of a magnetic resonance system 10 (MR system), with which in accordance with the invention MR images of a cyclically moving examination object can be recorded and can be calculated with the deformation information. The magnetic resonance system 10 has a scanner 11 in which a polarization field B0 is generated, wherein an examination person 13 on a bed 12 is moved into the center of the scanner 11, in order to acquire spatially graded magnetic resonance signals from an examination object with an RF coil (not shown) of the scanner 11. By radiating radio frequency pulse sequences and switching magnetic field gradients with a gradient coil arrangement of the scanner 11, the magnetization generated by the polarization field B0 can be deflected from the equilibrium position and the resulting magnetization can be detected with at least one reception coil (not shown) of the scanner 11. Moreover, spatial magnetization patterns such as a checked or striped pattern can be generated for instance with RF transmit coils (not shown) in the examination object. Methods of this type for generating magnetization patterns are also referred to as tagging methods. It is known to those skilled in the art how to generate such patterns in the magnetization by radiating special RF pulses, and thus need not be described in more detail herein. Such basic operation is described in Fischer SE et al in Magn. Reson. Med. 1993, 30: 191-200 or Osman N F et al, Magn. Reson. Med. 2001, 46: 324-334.

The general mode of operation for creating magnetic resonance images by the sequence of RF pulses on the magnetic field gradient is likewise known to those skilled in the art and need not be explained herein in more detail. The MR system 10 further has a central controller 20, which is used to control the MR device. The central controller 20 has an RF control processor 14 for controlling and switching the RF pulse in order to design the magnetization. A gradient control processor 15 is provided to control and switch the necessary magnetic field gradients. An image recording processor 16 controls the image recording with the detection of the MR signals and thus controls, as a function of the selected imaging sequence, the sequence in which the magnetic field gradients and RF pulses are used. This means that the image recording processor 16 also controls the gradient control processor 15 and the RF control processor 14. A person can control the course of the MR system 10 via an input interface 17, and the MR images can be indicated on a display monitor 18. A computer 19 is provided that, as explained in detail below, can perform a segmentation of the MR images and can calculate an item of deformation information from the segmented MR images. The imaging sequences required to record the MR images as well as other programs which are required to operate the MR system can be stored for instance in a storage unit 21.

FIG. 2 is a schematic representation of the MR images of the myocardium that were recorded in an EKG-triggered manner, wherein the individual MR images 22 and 23 were either recorded such that all required MR raw data was read out after a single RF excitation (so-called signal-shot technique). It is likewise possible for the MR recordings to have been recorded in a segmented recording technique in which k-space is subdivided into different segments and each segment is recorded with the same heartbeat phase. It is possible to record so-called recordings in the cine mode, in which a number of MR images are recorded during the cyclical movement. The MR image 22 is a segmented earlier MR image here, while the MR image 23 is a segmented subsequent MR image. This means that the MR signal recording was recorded during at least two cycles of the heart movement, wherein a number of MR images were recorded in each cycle. Prior to recording the MR images, a spatial magnetization pattern was generated with spatial magnetization differences in the examination area, as is apparent from the grid-type pattern 25 in the examination object. The MR image 22 or 23 is to schematically represent the heart with the myocardium 26. As can be seen from the comparison of the MR images 22 and 23, the magnetization pattern 25 in the MR image of the earlier of the at least two cycles can be identified more significantly. Since the magnetization with the T1 time and thus also the magnetization pattern approaches the equilibrium state, the magnetization pattern 25 in the MR image is lower in the subsequent cycle of the at least two cycles. Overall, more images can be recorded during more than two cycles, wherein the number of cycles depends in particular on the length of time the examination person is able to hold his/her breath.

The MR images of the earlier cycle are recorded briefly after generating the magnetization pattern, while the MR images of the subsequent cycle of at least one or a number of cycles are recorded subsequently. A segmentation can now take place more easily in the MR images of the subsequent cycle since the magnetization pattern which was generated in the examination object is only minimal and the edges can thus be better detected. This means that a simpler segmentation is possible in the MR images of the subsequent cycle. It is possible to determine the segmented subsequent MR image, in which, as shown in the segmented subsequent MR image 23, the myocardium was segmented. Known segmentation algorithms can be used here, which are based for instance on edge detection or other methods.

FIGS. 2 and 3 show how an item of radial deformation information and how a deformation in the peripheral direction, are determined from the number of segmented subsequent MR images 23 and from the segmented earlier MR images in each case. Since the edges in the MR image of the subsequent cycle can be easily identified, the segmented myocardium 26 is easy to determine. A radial deformation like the radial deformation 27 (see FIG. 5) from the segmented subsequent MR images can now be calculated from the movement of the edges during the cycle. This is possible for instance for various segments 28 of the myocardium, as is apparent from the dashed subdivision into different segments 28 in FIG. 3. It is thus possible to determine a reliable radial deformation from the segmented subsequent MR images. The segmentation information, i.e. the delimitation of the myocardium from surrounding tissue, can now be transferred to the MR images of the earlier cycle. Here the segmentation can be transferred to the MR images of the earlier cycle, by the number of MR images easily being subdivided into different segments during a cycle and the segmentation from the subsequent cycle being transferred to the segmentation of the earlier cycle for the same segment, i.e. to an MR image of the earlier cycle, which was recorded in the same time frame after the R-wave of the EKG. It is thus possible to transfer the segmentation information of the MR images of the subsequent cycle to the MR images of the earlier cycle. A further possibility is to use the similarity of the deformation fields which are calculated from the MR images of the earlier cycle and the subsequent cycle.

In FIG. 3, the segmented myocardium is highlighted separately to the left, as was determined from the MR images of the earlier of the two cycles, taking into account the segmentation information of the MR image of the subsequent cycle. The segmented earlier MR image now has another stronger magnetization pattern. It is thus possible to calculate the deformation 29 in the peripheral direction for the myocardium overall or for individual segments 28. The magnetization pattern can be generated by standard tagging methods or by phase-based methods such as DENSE. A gradient echo sequence, an SSFP (steady-state free precession gradient echo sequence) or an echo planar imaging sequence can be used as an imaging sequence.

It is further possible to calculate an item of combined deformation information, i.e. an overall deformation field, from the radial deformation information 27 and the deformation information in the peripheral direction 29. A weighted combination of the two deformation fields can be determined here, wherein the weighting includes being able to calculate the certainty with which the different deformation components can be calculated. The simplest assumption would be that only the one or the other component can be influenced binarily in each case. The precision of the two methods could also be derived from consistency considerations, such as conservation of mass and elasticity properties. Moreover, the consistency of the two items of deformation information can be improved by iterative methods such as total variation methods. An identical imaging sequence can be used for both MR images of the earlier and subsequent cycle. Moreover, it is possible to use different imaging sequences, for instance a so-called spoilt gradient echo sequence for a good contrast in the MR images of the earlier cycle and a gradient echo sequence with SSFP in the MR images of the subsequent cycle for the best anatomical contrast.

Moreover, the measurement of the deformation information can take place with volume or 3D MR sequences, which were recorded in a free breathing movement for instance with the navigator technique, so that it is known which breathing state is associated with which images.

The method is summarized in FIG. 4. The magnetization pattern is firstly created in the examination object in step 40. This creation can take place in any manner of spatial modulations of the magnetization. As a pattern, as in FIGS. 2 and 3, a grid-type pattern can be used, but other patterns such as simple lines, periodic lines or polar lines are also possible. The MR data is recorded in step S41 through a number of cycles of the cyclical movement. The cyclical movement may be the heart beat in the case of a heart, but other periodic cyclical organs such as the liver may also be used, or the vessel walls of larger vessels, which likewise move cyclically with the heartbeat.

After step S41, earlier MR images are thus present, which originate from an earlier of the at least two cycles, and subsequent MR images, which originate from a subsequent of the at least two cycles, wherein the magnetization pattern is more clearly highlighted in the earlier MR images than in the subsequent MR images, since the magnetization pattern approaches the equilibrium state on account of the T1 time of the magnetization. In step S42, the MR images of the subsequent cycle can be segmented, as shown in the right image in FIGS. 2 and 3. The segmentation in the MR images of the subsequent cycle is easily possible, since the anatomic information is easier to identify here on account of the smaller magnetization pattern. In step S43, at least the radial deformation or deformation at right angles to the segmentation lines, which result during the segmentation of the MR image as boundary lines to other tissue types, can be determined from the segmented MR images of the subsequent cycle, which in the case of the myocardium is the radial deformation. The segmented MR images or segmentation information obtained from the MR images of the subsequent cycle can be transferred to the MR images of the earlier cycle, as explained above in conjunction with FIGS. 2 and 3 (step S44). Since segmented earlier MR images now also exist, it is possible to determine the deformation at right angles to the existing deformation information, here the deformation in the longitudinal direction or parallel to the segmentation lines of the myocardium. This is possible in the segmented earlier MR images, since sufficient evidence which allows a determination of the deformation direction in the longitudinal direction (step S45) is present on account of the still existing magnetization pattern.

An item of deformation information thus can be easily determined in different spatial directions from a single signal recording after exciting the magnetization and generating the magnetization pattern.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining an item of deformation information from an examination subject that executes a cyclical movement in a magnetic resonance (MR) scanner, comprising:

operating an MR scanner, while an examination subject exhibiting a cyclical movement is situated therein, said cyclical movement causing a deformation of an examination object in said examination subject, so as to generate a spatial magnetization pattern, with spatial magnetization differences, of a magnetization of nuclear spins in the examination subject, said spatial magnetization pattern subsiding in strength over time after being generated;

operating the MR scanner, during at least two cycles of the cyclical movement that include an earlier cycle and a subsequent cycle that occurs at any time after said earlier cycle, to acquire MR signals from the examination subject, after generating the spatial magnetization pattern, that are dependent on said magnetization of said nuclear spins;

providing said MR signals to a computer and, in said computer, reconstructing an earlier MR image of the examination subject from the MR signals acquired during said earlier cycle, and reconstructing a subsequent MR image of the examination subject from the MR signals acquired during said subsequent cycle, said magnetization pattern being more weakly represented in said subsequent MR image in said earlier MR image due to said subsiding of said magnetization pattern;

said computer, determining a segmented subsequent MR image from said subsequent MR image in which said examination object in the examination subject is localized;

in said computer, using the examination object localized in said segmented subsequent image to determine a segmented earlier MR image from said earlier MR image in which the examination object localized in said segmented subsequent MR image is localized; and in said computer, determining, from the segmented earlier image, an item of deformation information that describes deformation of the examination object in a spatial direction.

2. A method as claimed in claim 1 wherein said item of information is a first item of information and wherein said spatial direction is a first spatial direction, and comprising, in said computer, determining, from the segmented subsequent MR images, a second item of deformation information that describes deformation of the examination object in a second spatial direction that differs from said first spatial direction.

3. A method as claimed in claim 2 comprising, in said computer, determining an overall deformation field of the examination object from said first item of deformation information and said second item of deformation information.

4. A method as claimed in claim 1 comprising operating said MR scanner to acquire said MR signals during said earlier cycle with a first MR imaging sequence and operating said MR scanner to acquire said MR signals during said subsequent cycle with a second MR imaging sequence that differs from said first MR imaging sequence.

5. A method as claimed in claim 1 wherein said examination object is the myocardium of the examination subject, and wherein said item of deformation information describes a deformation of the myocardium in a peripheral direction of the myocardium.

6. A method as claimed in claim 5 wherein said item of deformation information is a first item of deformation information, and comprising determining a second item of deformation information using the segmented subsequent MR images in a spatial direction that differs from said peripheral direction, said second item of information describing a radial deformation of the myocardium.

7. A method as claimed in claim 6 wherein determination of one of the segmented earlier images takes place for an MR image of the earlier cycle, in which the deformation information associated with the MR image of the earlier cycle is determined, and the MR image having the determined deformation information from the MR image of the earlier cycle is most similar is identified from the item of information in the segmented subsequent MR images, and wherein an item of information is determined from the segmented subsequent MR image and is transferred to the MR image of the earlier cycle with the most similar deformation information.

8. A method as claimed in claim 6 comprising determining a monitoring signal that associates a passage of time with said cyclical movement of the examination object, and determining that one of the segmented earlier MR images for an MR image of the earlier cycle, by the segmented subsequent MR image being determined that was acquired during a same time frame, dependent on said monitoring signal, as the MR image of the earlier cycle, and determining an item of segmentation information from the segmented subsequent MR image and transferring said item of segmentation information to the MR image of the earlier cycle.

9. A method as claimed in claim 8 wherein said examination object is the myocardium of the examination subject and wherein said item of deformation information is a first item of deformation information that describes deformation of the myocardium in a peripheral direction, and determining a second item of information from the segmented subsequent MR images that describes deformation of the myocardium in a radial direction, by dividing the myocardium into multiple segments in the peripheral direction determining said second item of deformation information in the radial direction from a selected number of said multiple segments.

10. A method as claimed in claim 9 comprising determining, in said computer, an overall deformation field of the examination object from a weighted combination of said first item of deformation information and said second item of deformation information.

11. A magnetic resonance (MR) apparatus comprising:
an MR scanner;
a computer configured to operate the MR scanner, while an examination subject exhibiting a cyclical movement is situated therein, said cyclical movement causing a deformation of an examination object in said examination subject, so as to generate a spatial magnetization pattern, with spatial magnetization differences, of a magnetization of nuclear spins in the examination subject, said spatial magnetization pattern subsiding in strength over time after being generated;
said computer being configured to operate the MR scanner, during at least two cycles of the cyclical movement that include an earlier cycle and a subsequent cycle that occurs at any time after said earlier cycle, to acquire MR signals from the examination subject, after generating the spatial magnetization pattern, that are dependent on said magnetization of said nuclear spins;
said computer being configured to reconstruct an earlier MR image of the examination subject from the MR signals acquired during said earlier cycle, and reconstructing a subsequent MR image of the examination subject from the MR signals acquired during said subsequent cycle, said magnetization pattern being more weakly represented in said subsequent MR image in said earlier MR image due to said subsiding of said magnetization pattern;

said computer being configured to use the examination object localized in said segmented subsequent image to determine a segmented subsequent MR image from said subsequent MR image in which said examination object in the examination subject is localized;

said computer being configured to determine a segmented earlier MR image from said earlier MR image in which the examination object localized in said segmented subsequent MR image is localized; and said computer being configured to determine, from the segmented earlier image, an item of deformation information that describes deformation of the examination object in a spatial direction.

12. A non-transitory, computer-readable data storage medium encoded with programming instructions, said storage medium loaded into a computer of a magnetic resonance (MR) apparatus that comprises an MR scanner, and said programming instructions causing said computer to:

operate the MR scanner, while an examination subject exhibiting a cyclical movement is situated therein, said cyclical movement causing a deformation of an examination object in said examination subject, so as to generate a spatial magnetization pattern, with spatial magnetization differences, of a magnetization of nuclear spins in the examination subject, said spatial magnetization pattern subsiding in strength over time after being generated;

operate the MR scanner, during at least two cycles of the cyclical movement that include an earlier cycle and a subsequent cycle that occurs at any time after said earlier cycle, to acquire MR signals from the examination subject, after generating the spatial magnetization pattern, that are dependent on said magnetization of said nuclear spins;

reconstruct an earlier MR image of the examination subject from the MR signals acquired during said earlier cycle, and reconstructing a subsequent MR image of the examination subject from the MR signals acquired during said subsequent cycle, said magnetization pattern being more weakly represented in said subsequent MR image in said earlier MR image due to said subsiding of said magnetization pattern;

determine a segmented subsequent MR image from said subsequent MR image in which said examination object in the examination subject is localized;

use the examination object localized in said segmented subsequent image to determine a segmented earlier MR image from said earlier MR image in which the examination object localized in said segmented subsequent MR image is localized; and determine, from the segmented earlier image, an item of deformation information that describes deformation of the examination object in a spatial direction.

* * * * *